United States Patent

Yanof et al.

[11] Patent Number: 6,149,592
[45] Date of Patent: Nov. 21, 2000

[54] INTEGRATED FLUOROSCOPIC PROJECTION IMAGE DATA, VOLUMETRIC IMAGE DATA, AND SURGICAL DEVICE POSITION DATA

[75] Inventors: Jeffrey H. Yanof, Solon; Pieter Gerhard Roos, Bainbridge; Kenneth L. Freeman, Stow; Joseph S. Deucher, Lyndhurst; Andrew J. Ivan, Reminderville; Dominic J. Heuscher, Aurora, all of Ohio

[73] Assignee: Picker International, Inc., Highland Heights, Ohio

[21] Appl. No.: 08/980,171

[22] Filed: Nov. 26, 1997

[51] Int. Cl.[7] .................................................. A61B 5/00
[52] U.S. Cl. ............................................ 600/427; 606/130
[58] Field of Search ................................... 600/424, 425, 600/429, 427; 606/130; 378/190, 196, 205, 206

[56] References Cited

U.S. PATENT DOCUMENTS

| | | |
|---|---|---|
| 4,750,487 | 6/1988 | Zanetti . |
| 4,791,934 | 12/1988 | Brunnett . |
| 5,099,846 | 3/1992 | Hardy ..................................... 128/653.1 |
| 5,129,911 | 7/1992 | Siczek et al. . |
| 5,408,409 | 4/1995 | Glassman et al. . |
| 5,622,170 | 4/1997 | Schulz ................................... 128/653.1 |
| 5,662,111 | 9/1997 | Cosman . |
| 5,734,384 | 3/1998 | Yanof et al. . |
| 5,772,594 | 6/1998 | Barrick . |
| 5,799,055 | 8/1998 | Peshkin et al. . |
| 5,841,830 | 11/1998 | Barni et al. . |
| 5,978,696 | 11/1999 | VomLehn et al. ....................... 600/411 |
| 6,006,126 | 12/1999 | Cosman .................................. 600/426 |
| 6,006,127 | 12/1999 | Van Der Brug et al. ............... 600/427 |
| 6,026,315 | 2/2000 | Lenz et al. ............................. 600/414 |
| 6,035,228 | 3/2000 | Yanof et al. ............................ 600/429 |
| 6,041,249 | 3/2000 | Regn ...................................... 600/429 |

*Primary Examiner*—Marvin M. Lateef
*Assistant Examiner*—Shawna J. Shaw

[57] ABSTRACT

A patient supported on a patient support (12) is moved into a bore (22) of a planning imaging device, such as a CT scanner (20). A three-dimensional diagnostic image in three-dimensional diagnostic image space is generated and stored in a memory (130). The patient is repositioned outside of the bore with a region of interest in alignment with a real time imaging device, such as a fluoroscopic imaging device (40). A surgical planning instrument (60), such as a pointer or biopsy needle (62), is mounted on an articulated arm (64). As the instrument is inserted into the region of interest, fluoroscopic images are generated and stored in a memory (140). The coordinate systems of the CT scanner, the fluoroscopic device, and the surgical instrument are correlated (102, 104, 112, 120) such that the instrument is displayed on both the CT images (134) and the fluoroscopic images (50), such that cursors move concurrently along the fluoroscopic and CT images, and the like. In a preferred embodiment in which the cursor on the CT image display is at an intersection of transverse, sagittal, and coronal planes, the displayed planes change as the cursor moves coordinating the displayed CT image planes with the position of the cursor on the fluoroscopic image.

21 Claims, 3 Drawing Sheets

INTEGRATED FLUOROSCOPIC PROJECTION IMAGE DATA, VOLUMETRIC IMAGE DATA, AND SURGICAL DEVICE POSITION DATA

BACKGROUND OF THE INVENTION

The present invention relates to the medical diagnostic imaging and minimally invasive surgery arts. It finds particular application in conjunction with an integrated CT scanner, fluoroscopic x-ray device, and mechanical arm type minimally invasive type surgical tool and will be described with particular reference thereto. It is to be appreciated, however, that the invention is also applicable to magnetic resonance imaging and other imaging systems capable of generating volumetric images. The system is also applicable to other real time imaging systems capable of monitoring a region of the patient during a minimally invasive surgical procedure. The invention is also applicable to performing surgical procedures with minimally invasive surgical instruments whose position is monitored using electronic triangulation techniques rather than a mechanical arm.

Heretofore, volumetric image data of patients have been generated using CT scanners, magnetic resonance imagers, and the like. The 3D image data has been used to plan minimally invasive and other surgical procedures. However, the bulky size of the CT scanners and magnetic resonance imagers, the data acquisition time, radiation in CT scanners, strong magnetic fields in magnetic resonance imagers, and the like, render such imagers inconvenient for monitoring minimally invasive or other surgery in real time. More typically, a minimally invasive procedure might be planned based on such diagnostic images and carried out at a later time.

At one or more points during the invasive procedure, the procedure might be stopped and the patient reintroduced into the imager to determine whether the surgical instrument has reached the target, is following the appropriate trajectory, or the like. Such starting and stopping of the surgical procedure, movement of the patient, and the like is again inconvenient and can introduce error. Moreover, such a system checks the surgical procedure after the fact and does not provide real time monitoring.

Minimally invasive surgical procedures have been monitored using fluoroscopic projection equipment. During the interventional surgical procedure, the surgeon actuates the fluoroscopic equipment from time to time to generate projection images of the region of interest and the surgical instrument. However, in fluoroscopic images, data from the entire subject is projected or compressed into a single plane. This permits the position of the surgical device to be monitored relative to the two axes in the plane of the image but provides limited queues as to the depth in the direction perpendicular to the image. Moreover, fluoroscopic images are typically at relatively low radiation doses and have less resolution than CT or MRI images.

Some interventionalists display images derived from the volumetric data on one monitor concurrently with the display of fluoroscopic images on another monitor. The data on the two images is integrated in the interventionalist's mind. Such mental integration raises the prospect of mental mistake and judgement errors.

The present invention provides a new and improved method and apparatus which overcomes the above-referenced problems and others.

SUMMARY OF THE INVENTION

In accordance with one aspect of the present invention, a method of minimally invasive surgery is provided. A region of interest of a patient is imaged using a three-dimensional diagnostic imaging technique to generate volumetric image data. As a surgical probe is inserted into the region of interest, a series of fluoroscopic projection images of the region of interest and the instrument are generated to monitor movement of the surgical instrument. The volumetric image data is generated and displayed in a volumetric image coordinate system; and the fluoroscopic images are generated and displayed in a fluoroscopic image coordinate system. The fluoroscopic image coordinate system and the volumetric image coordinate system are electronically correlated.

In accordance with another aspect of the present invention, a method of minimally invasive surgery is provided. A medical diagnostic planning image is generated of a region of interest in a patient. A minimally invasive surgical procedure is planned based on the planning image. The patient is positioned for the surgical procedure in association with a substantially real time imaging device which is positioned and selectively actuatable to generate images of the region of interest substantially in real time. A mathematical transform between a coordinate system of the real time images and a coordinate system of the planning image is derived. During the surgical procedure, real time images of the region of interest are generated, which real time images include an inserted portion of a surgical instrument. Coordinate positions of the surgical instrument are transformed into corresponding coordinates of the planning image. An image representation of the surgical instrument at corresponding coordinates of the planning image is generated.

In accordance with another aspect of the present invention, a medical diagnostic imaging and minimally invasive surgical system is provided. A surgical planning instrument is movable by an operator to any of a plurality of locations adjacent to and in a region of interest of a subject. A system generates electrical signals indicative of coordinates of the instrument in instrument space. A three-dimensional diagnostic imaging apparatus generates three-dimensional diagnostic image data which is indicative of anatomical structure of the subject in three-dimensional image space. A three-dimensional diagnostic image memory stores the generated three-dimensional diagnostic image data. A real time imaging device generates real time image data of the region of interest in real time image space. A transform processor transforms at least one coordinate of the surgical instrument into the three dimensional image space. At least one human-readable display is connected with the transform processor, the three-dimensional image data memory, and the real time imaging device for generating a human-readable display of a real time image and at least one of (i) slices of the three-dimensional imaging data which slices intersect at the transformed coordinate and (ii) an image generated from the three-dimensional image data with a representation of the surgical instrument superimposed thereon.

One advantage of the present invention is that it enables surgery to be monitored in real time.

Another advantage of the present invention resides in its accurate combining of surgical instrument position with previously generated volumetric diagnostic images.

Another advantage of the present invention is that it integrates real time images with previously collected diagnostic images.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
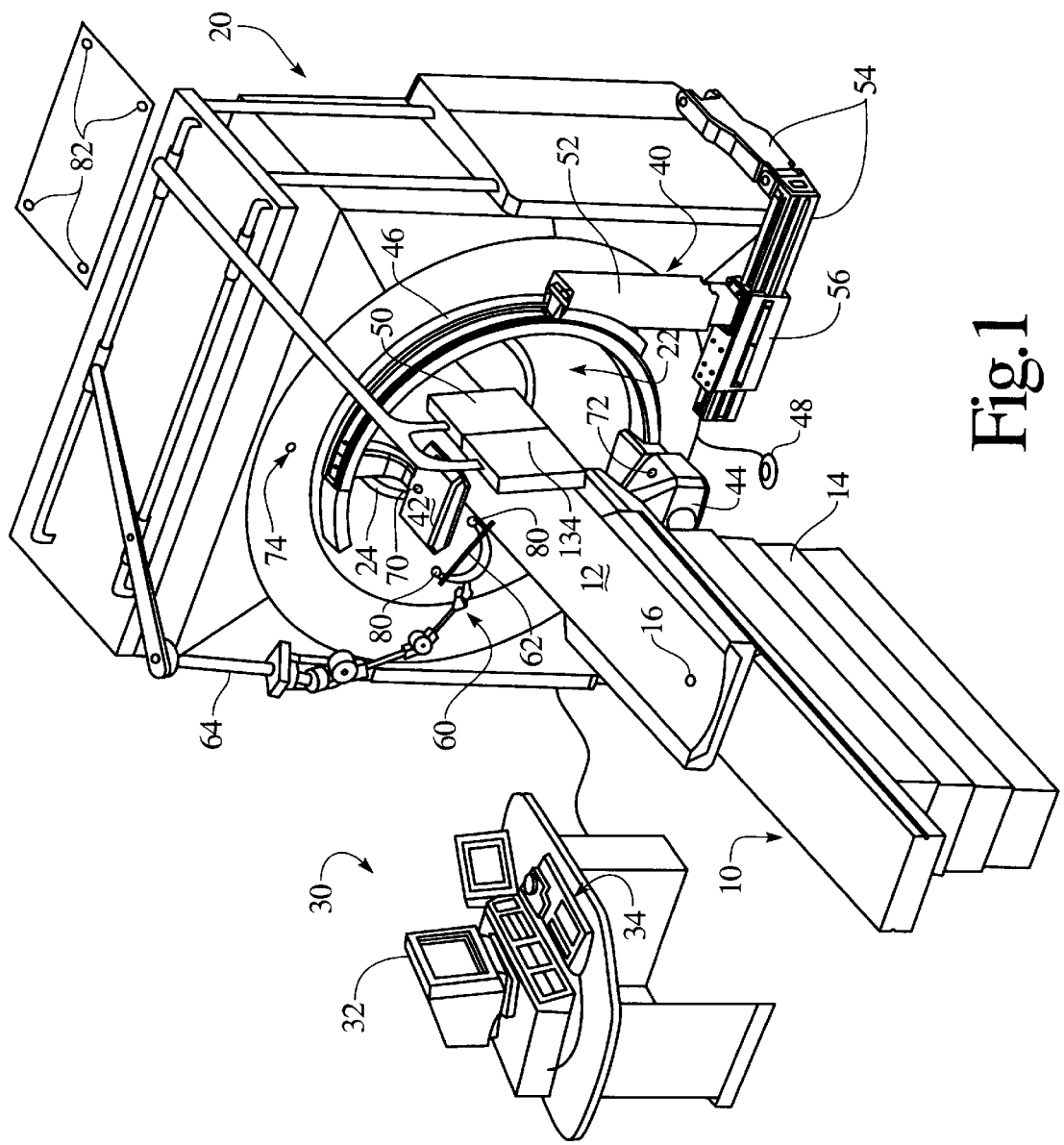
FIG. 1 is a diagrammatic illustration of a CT scanner, fluoroscopic system, and minimally invasive surgical arm in accordance with the present invention.

With reference to FIG. 1, a patient table or support 10 includes a patient supporting surface 12 that is mounted for longitudinal movement relative to a base portion 14. The base portion 14 includes a motor for raising and lowering the patient support surface 12 and for moving the patient support surface longitudinally. Position encoders are also provided for generating electrical signals indicative of the height and longitudinal position of the patient support. The patient support includes a calibration marker 16 disposed at a known, fixed location.

A planning, preferably volumetric diagnostic imaging apparatus 20 is disposed in axial alignment with the patient table such that a patient or subject on the patient support surface 12 can be moved into and through a bore 22 of the volumetric imager. In the illustrated embodiment, the volumetric imager is a CT scanner which includes an x-ray tube mounted for rotation about a preselected plane. The x-ray tube projects a fan-shaped beam of radiation through a ring 24 of radiation translucent material, through the patient support 12, through a region of interest of the subject, and to a ring or arc of radiation detectors positioned opposite the x-ray tube. As the x-ray tube rotates within the plane, a series of data lines are generated, which data lines are reconstructed into at least a slice image by a reconstruction processor included-in a control console 30. More specifically to the preferred embodiment, the patient support 12 moves longitudinally as the x-ray tube is rotating around the subject such that a selected volume of the patient is scanned along a spiral path or a series of slices. The position of the x-ray tube is monitored by a rotational position encoder, the longitudinal position of the patient support is monitored by a longitudinal position encoder within the couch 10. The reconstruction processor reconstructs a volumetric image representation from the generated data lines. The control console typically includes one or more monitors 32 and an operator input device 34, such as a keyboard, trackball, mouse, or the like.

A fluoroscopic imaging system 40 is mechanically mounted to the planning image scanner 20. More specifically to the preferred embodiment, a flat plate x-ray detector 42 and an x-ray tube 44 are mounted in a cantilevered manner to 180° opposite points on a C-arm 46. When the x-ray tube is actuated by depressing a foot pedal 48, a beam of x-rays is projected through the patient support 12, through the subject on the patient support, and onto the x-ray detector 42. The x-ray detector 42 converts the x-rays into electronic signals which are used to generate human-readable, real time displays on a video monitor 50. Other real time or substantially real time imaging systems are also contemplated, such as continuous CT (CCT), and the like.

The C-arm 46 is rotatably mounted to a support post 52. An encoder in the support post encodes its rotational position as it is rotated manually or by motor around a plane of rotation. A mechanical linkage, such as a pair of pivotally interconnected arms or links 54 enable the fluoroscopic device to be pivoted into the illustrated position and pivoted to the side of the volumetric imager for storage. A sliding member 56 is movable manually or by motor along one of the arms parallel to the plane of rotation. A position encoder encodes the position of the support along the arm, hence horizontal displacement of a center of rotation of an x-ray source and detector. The mechanical interconnections are such that the plane of rotation of the fluoroscopic x-ray source and detectors is parallel to the plane of rotation of the CT scanner x-ray source and perpendicular to a longitudinal axis of the patient support. Moreover, the mechanical interconnection between the fluoroscopic device and the CT scanner provides a precisely fixed and known offset between the two planes of rotation.

A minimally invasive planning surgical instrument 60 is positioned by the operator in monitored positions and orientations in preparation for and in carrying out a surgical procedure. The surgical planning instrument in the illustrated embodiment includes a manually guided biopsy needle 62, although numerous other instruments are contemplated. The position and orientation of the instrument are determined by a mechanical arm assembly 64. The mechanical arm assembly includes a plurality of arm segments which are interconnected by pivot members. Encoders or position resolvers at each joint monitor the relative articulation and rotation of the arms relative to each other. Position encoders or resolvers are also provided along the mechanical interconnection of the arm with the CT scanner. In this manner, the mechanical interconnection which is measured by the resolvers and encoders provides an accurate indication of the position and orientation of the instrument 62 relative to the CT scanner. Because the fluoroscopic system is also mechanically constrained to monitored orientation relative to the CT scanner, the position and orientation of the instrument 60 is also known relative to the fluoroscopic system.

To verify the relative orientation and position of the surgical instrument relative to the patient support, a tip of the surgical instrument or pointer is touched to the calibration marker 16 and an assessment is made whether the electronic signals indicative of patient support location and surgical instrument location, in fact, place both at the same point in space. Analogously, one or more reference markers 70, 72 are mounted at known locations to the fluoroscopic device. Again, touching the tip of the surgical instrument or pointer to these markers enables verification of their relative positions. Similarly, one or more markers 74 on the CT scanner in a fixed, known location relative to the plane of rotation of the x-ray beam is touched by the tip of the surgical instrument or pointer and the electronic positions signals are compared to be sure that the coordinate systems of the volumetric scanner and the surgical instrument are accurately correlated.

Other mechanisms for monitoring the position of the surgical tool or pointer 62 are also contemplated. For example, a plurality of transmitters, such as light emitting diodes 80 are mounted in a fixed, known relationship to the surgical tool or pointer. An array of receivers 82 is mounted in a fixed relationship to the CT scanner, preferably affixed to the ceiling of the room. Each time the emitters are actuated and the emitted signal received by the receivers, the position and orientation of the planning instrument are accurately and quickly calculated using geometric triangulation techniques. By positioning the planning instrument on a plurality of markers, preferably 3 or more, e.g. markers 70 or 72 which are mounted in a fixed, known relationship to the coordinate system of the fluoroscopic scanner, the planning instrument coordinate system and the fluoroscopic coordinate system can be readily aligned. Analogously, by touching the planning instrument to the plurality of markers 74 disposed in a known, fixed relationship to the coordinate system of the CT scanner, the coordinate systems of the planning instrument and CT scanner can be readily correlated. Analogously, by positioning the planning instrument on marker 16 on the patient table, the coordinate system of the planning instrument and patient table can be readily coordinated.

Figure 2:
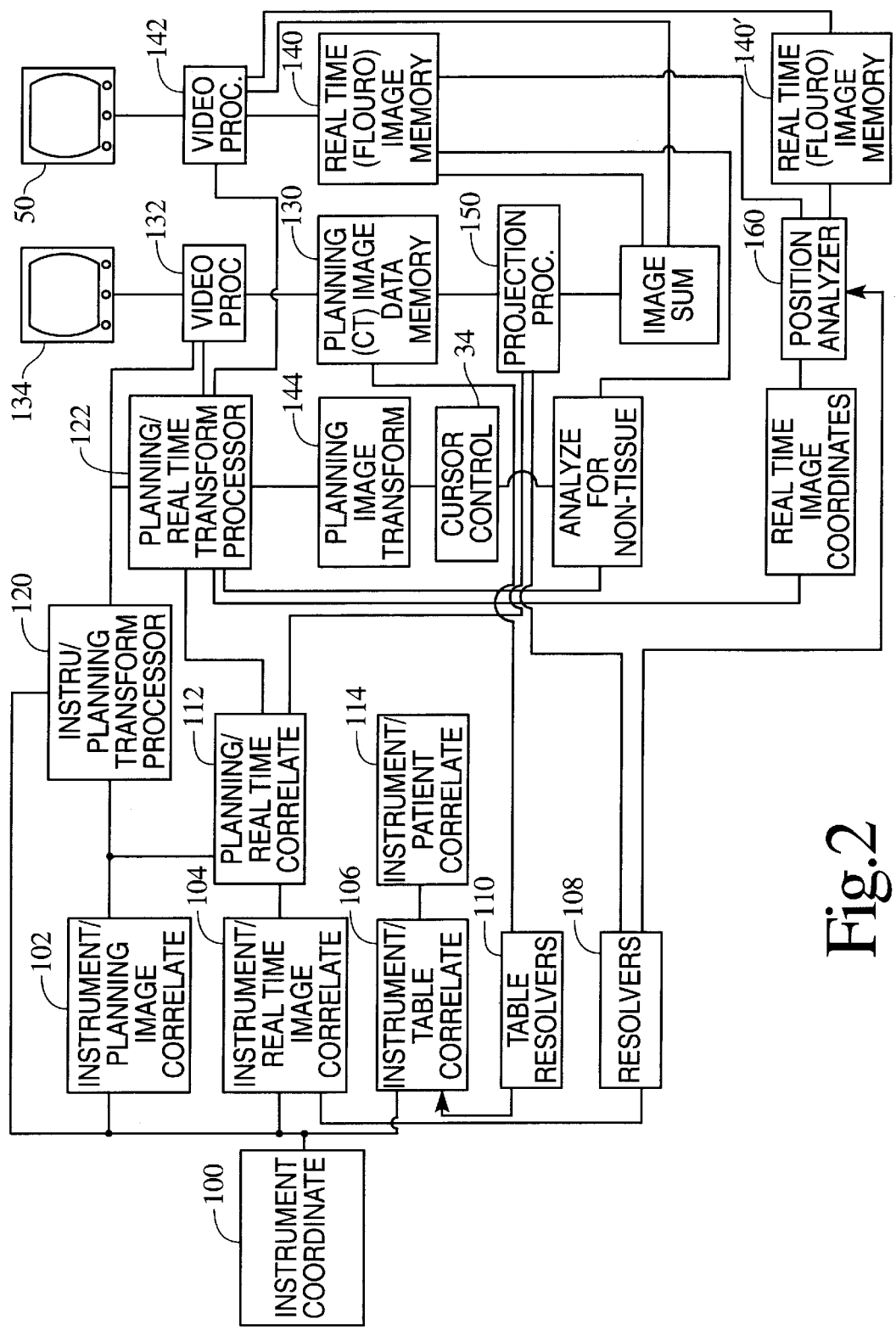
FIG. 2 is a diagrammatic illustration of real time and planning image processing performed with the apparatus of FIG. 1; and, FIG. 3 is a diagrammatic illustration illustrative of resolving three-dimensional position information from a pair of angularly offset fluoroscopic images.

With reference to FIG. 2, an instrument coordinate circuit 100 determines the position and trajectory of the biopsy needle 62 in instrument space, particularly a coordinate system of the instrument. The instrument coordinate circuit is connected with the resolvers on the mechanical arm 64 in the mechanical arm embodiment and with the receivers 82 in the emitter embodiment to receive signals indicative of changes of position and orientation of the instrument in instrument space. An instrument-planning scanner correlating processor 102 determines the correlation or transform between the biopsy needle 62 and the volumetric scanner 20 coordinate systems. The correlation or transform is normally described in terms of offset (particular offset along the axis of the patient support), angular offset or rotation, and scaling. In one embodiment, the instrument 62 is touched to three or more markers 74 which are in a known relationship to the volumetric scanner coordinate system. By measuring the coordinates of the instrument in the instrument coordinate system while touching each marker, three or more common points in the two coordinate systems are determined. By determining a barrycenter, centroid, or other characteristic point of the common points, the offset between the two coordinate systems is determined. By determining the angular difference between the rays from the characteristic point to each point in each coordinate system, the angular offset is determined. By determining a difference in physical displacement between the characteristic point and the corresponding points in each coordinate system, the scaling factor is determined. Of course, in a system such as the illustrated embodiment in which the instrument and the volumetric scanner are mechanically linked, the transform or relationship between the volumetric scanner and instrument coordinate systems can be predetermined from the mechanical interconnection. The touching of markers can be eliminated or used merely to confirm that the instrument and CT scanner coordinates have not become misaligned.

Using analogous mathematics or known mechanical relationships, an instrument to fluoroscopic device correlation processor 104 determines the correlation or transform between the instrument and fluoroscopic device coordinate systems. An instrument to patient table correlating processor 106 performs a similar calculation or uses similar known physical relationships to determine the correlation or transform between the patient table and the instrument. Preferably, a phantom having a multiplicity of marks is positioned in a known position on the table to provide a larger number of corresponding points in both coordinate systems for the correlating process. Images of the phantom can be utilized to derive transforms between patient table space and planning or real time image coordinate systems.

Resolvers 108 located in the arm 52 of the fluoroscopic device contribute an angular offset to the fluoroscopic device to instrument correlation or transform when the C-arm including the x-ray source and detector are rotated and provide a vertical offset when the arm 52 is raised or lowered. Analogously, table resolvers 110 located in the patient table contribute vertical and longitudinal offsets to the correlation between the instrument and the patient table when the table is raised or lowered and when the patient support 12 is moved axially. A planning to real time, i.e., a volumetric to fluoroscopic coordinate system correlation processor 112 determines a correlation between the volumetric scanner and the fluoroscopic scanner coordinate systems. Because the transforms are linear operators, the transform between the instrument and volumetric scanner and the transform between the instrument and the fluoroscopic device coordinate system can be simply combined. Optionally, an instrument to patient correlation processor 114 determines the correlation between the instrument coordinate system and a patient coordinate system. Again, this can be done by placing the instrument on three or more known reference points on the patient. Such points might include readily identifiable anatomical structures such as the tip of the nose, distinctive points on bones, fiducial markers that are imaged during the volumetric or fluoroscopic imaging process, or the like.

An instrument to volumetric image coordinate system transform processor 120 receives the correlation or transform from the instrument to planning image processor 102. The instrument to volumetric image processor operates on input position and orientation coordinates in image space to transform them into volumetric image data space or vice versa. Knowing the position of the instrument in volumetric or planning data space enables the instrument position and orientation to be superimposed on the volumetric planning image data. Analogously, a planning image to real time image transform processor 122 operates on input coordinates in one of the planning and fluoroscopic coordinate systems to generate the corresponding position and trajectory coordinates in the other.

During a medical procedure, the patient is positioned in the volumetric planning scanner and a volumetric image is generated. The volumetric image is stored in a volumetric or planning data memory 130. The position of the patient table during the generation of the planning data, particularly as the table moves to generate spiral or slice data, is stored in conjunction with the volumetric planning data such that the data is correlated with the patient table coordinate system. The operator control 30 controls the volume planning image data memory or a video processor 132 such that selected slices, projection images, surface renderings, or other conventional displays of the data are generated for display on a planning image display 134. Preferably, the planning image display includes corresponding sagittal, coronal, and traverse slices through a common point of intersection. Analogously, the real time fluoroscopic x-ray tube 44 is actuated to generate an x-ray beam that is detected by the x-ray detector 42 to generate a real time image which is stored in a real time image memory 140. A video processor 142 converts the real time image into appropriate format for display on the real time fluoroscopic image display 50.

The fluoroscopic device's x-ray beam has a center line that can be aligned with a target in the patient. The surgical instrument is positioned on and inserted along the center line while watching the volume display in three-dimensional space or the fluoroscopic display in two-dimensional space.

Because the fluoroscopic display is generated during the surgical procedure, the instrument is displayed in the fluoroscopic image. The coordinates and trajectory of the instrument are conveyed to the instrument to planning image transform processor 120 for conversion into the planning image coordinate system. The location and trajectory of the instrument in the planning image coordinate system is communicated to the video processor 132 which superimposes the surgical instrument position and trajectory on the CT data display. The operator control 34, preferably a trackball or mouse, generates cursor position signals which are transformed into the planning image coordinate system 144 and communicated to the video processor 132 to generate a movable cursor point on the planning image display 134. The same coordinates are also communicated to the planning image to real time image transform processor 122 to be transformed into the real time image coordinate system and to the video processor 142 to be superimposed on the fluoroscopic image. In this manner, the cursor is positioned at like points in both displays.

In one embodiment, a projection processor 150 projects the volumetric image data from the planning image memory 130 along selected orientations. More specifically, the projection processor 150 is connected with the planning to real time (volumetric to fluoroscopic) coordinate system correlation processor 112 or the fluoroscopic device resolvers 108 in order to generate the same projection as is currently displayed on the fluoroscopic display 50. An image superimposition or summing processor 152 superimposes, sums, or otherwise combines the projected volumetric image and the fluoroscopic image and provides these summed image signals to the video processor 142 for display on the monitor 50. In this manner, higher and lower resolution projection images are combined to improve the apparent resolution. As the C-arm is rotated, the projection processor 150 reprojects the volumetric image along the new direction. Alternately, the two images can be displayed side by side, subtracted, or the like.

Figure 3:
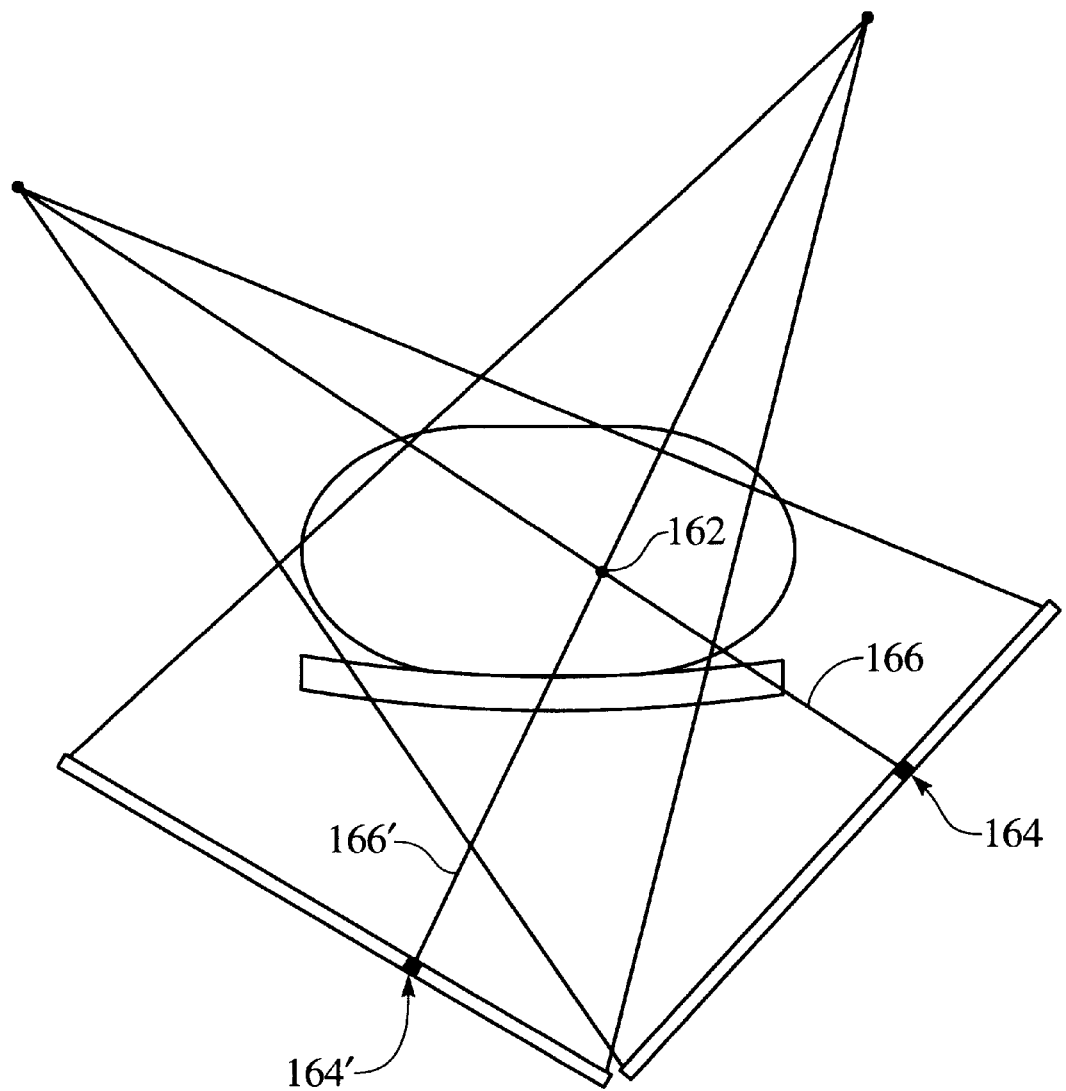

In another embodiment, during a surgical procedure, the instrument is moved to a location in the patient while monitoring the fluoroscopic image. To check its exact position, the C-arm 46 is rotated several degrees, preferably about 90° and a second fluoroscopic image 140' is generated. A position analyzing processor 160 analyzes the two angularly offset fluoroscopic images to determine the position and orientation of the instrument in three dimensions in the coordinate system of the fluoroscopic device. As illustrated by way of example in FIG. 3, a point 162 in the patient is projected as a spot 164 in the first fluoroscopic image and a spot 164' in the second fluoroscopic image. The spot 164 is projected along a ray 166 back to the origin at the x-ray source. Analogously, spot 164' is projected back along a ray 166' to the origin or x-ray source. These two rays intersect at the point 162, thus identifying the coordinates of the point 162. A large plurality of projection images can be backprojected to identify the coordinate. It will be appreciated that FIG. 3 illustrates only a single slice of the patient. However, because the projection images are two-dimensional, a multiplicity of such slices are analyzed concurrently to generate the coordinates in three dimensions in fluoroscopic image space. The coordinates indicative of the position and trajectory of the instrument are communicated to the volumetric to fluoroscopic coordinate system transform processor 122 to be converted into corresponding coordinates in planning volume image space and to the video processor 122 such that the surgical instrument is superimposed on the planning image data.

In another alternate embodiment, the cursor is positioned at the point of intersection of concurrently displayed transverse, coronal, and sagittal views on the volumetric image display 134. As the operator moves the cursor control 34 through volumetric image data space, the sagittal, coronal, and transverse views change corresponding. When the cursor is also displayed on the fluoroscopic display, moving the cursor through the fluoroscopic image causes the sagittal, coronal, and transverse views on the volumetric image display to change correspondingly.

It is to be appreciated that numerous other techniques can be utilized for correlating the above-discussed coordinate systems. For example, when two fluoroscopic images are generated, the images can be analyzed to determine the coordinates of fiducial markers, characteristic anatomical structures, or the like in fluoroscopic image space. The same points can then be identified in volume image space. An analogous correlation process to that discussed above can then be utilized to correlate fluoroscopic image and volumetric data space. When common fiducial markers are used in both the volumetric image and the fluoroscopic image, the fluoroscopic and volumetric images can be analyzed or windowed electronically to identify the corresponding markers. In this manner, the corresponding markers can be identified and correlated automatically without operator intervention. A similar operation can be done with anatomical markers, if the anatomical markers can be distinguished by the computer without operator intervention. Alternately, the procedure can be made semi-automatic requiring the operator only to identify the corresponding anatomical structures in all images.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A method of minimally invasive surgery comprising the steps of:
    imaging a region of interest of a patient using a three-dimensional diagnostic imaging technique to generate volumetric image data in a volumetric image coordinate system;
    as a surgical instrument is inserted into the region of interest, generating a series of fluoroscopic projection images of the region of interest including the surgical instrument in a fluoroscopic image coordinate system for monitoring movement of the surgical instrument into the region of interest;
    electronically correlating the fluoroscopic image coordinate system and the volumetric image coordinate system; and,
    displaying the volumetric image data together with at least a portion of said series of fluoroscopic images superimposed on the volumetric image data to show an image of said surgical instrument relative to said volumetric image data.

2. The method as set forth in claim 1 further including:
    monitoring the position of the surgical instrument in the fluoroscopic coordinate system;
    transforming the position of the surgical instrument from the fluoroscopic image coordinate system into the volumetric image coordinate system; and, displaying an indication of the surgical instrument in the volumetric image coordinate system superimposed on at least one volumetric image display.

3. The method as set forth in claim 1 further including:

generating a fluoroscopic image display;

generating a volumetric image display;

generating a cursor display on one of the fluoroscopic and volumetric image displays;

transforming a coordinate location of the cursor from the coordinate system of the one display into the coordinate system of the other display and displaying the cursor at the corresponding coordinate position in the other display such that the cursor is displayed at corresponding coordinate positions in both displays.

4. The method as set forth in claim 3 wherein the step of generating the volumetric image display includes displaying at least two of transverse, sagittal, and coronal slices which intersect at the cursor such that as the operator moves the cursor, at least one of the displayed transverse, sagittal, and coronal slices change.

5. The method as set forth in claim 1 further including:

generating at least two fluoroscopic projection images which are angularly displaced from each other;

analyzing the angularly displaced fluoroscopic projection images to determine at least one of a position and trajectory of the instrument in the fluoroscopic image coordinate system;

transforming the instrument location or trajectory from the fluoroscopic image coordinate system to the volumetric image coordinate system;

superimposing at least one of the instrument trajectory and position on the volumetric image.

6. The method as set forth in claim 1 further including:

projecting the volumetric image to generate a projection image;

transforming the projection image from the volumetric image coordinate system into the fluoroscopic image coordinate system; and displaying the transformed projection image in association with the fluoroscopic image.

7. The method as set forth in claim 1 in which the luoroscopic image is a projection along a first direction and further including:

projecting the volume image along the first direction to generate a projected volume image;

combining the fluoroscopic image and the projected volume image.

8. The method as set forth in claim 7 further including:

rotating the fluoroscopic image such that it is a projection along another direction;

projecting the volume image along the another direction; and combining the rotated fluoroscopic image and the volume image projected along the another direction.

9. The method as set forth in claim 1 wherein the correlating step includes:

correlating the volumetric image coordinate system with a coordinate system of an instrument to determine a volumetric image space/instrument space transform therebetween;

correlating the fluoroscopic image coordinate system with the instrument coordinate system to generate a fluoroscopic image space/instrument space transform therebetween;

combining the volumetric image space/instrument space transform with the fluoroscopic space/instrument space transform to generate a fluoroscopic space/volumetric image space transform for transforming directly between the fluoroscopic image coordinate system and the volumetric image coordinate system.

10. The method as set forth in claim 9 further including:

operating on a coordinate position of an instrument in instrument space with the volumetric image space/instrument space transform to generate a corresponding position coordinate in the volumetric image coordinate system; and superimposing a display of the transformed coordinate on a display of the volumetric image data.

11. The method as set forth in claim 9 further including:

generating a human-readable display of the fluoroscopic image data;

generating a human-readable display from the volumetric image data;

superimposing a cursor on one of the fluoroscopic and volumetric image displays;

transforming coordinates of the cursor using the fluoroscopic space/volumetric image space transform and generating a corresponding cursor display on the other image;

under operator control, moving the cursor coordinately in both images.

12. The method as set forth in claim 1 further including:

aligning a center line of the fluoroscopic image with a target in the patient while displaying the position of this centerline on the volume display;

inserting the surgical instrument along the center line.

13. A method of minimally invasive surgery comprising:

generating a medical diagnostic planning image of a region of interest in a patient;

planning a minimally invasive surgical procedure based on the planning image;

positioning the patient for the surgical procedure in association with a substantially real time imaging device which is positioned and selectively actuatable to generate images of the region of interest substantially in real time;

deriving a mathematical transform which transforms between a coordinate system of the real time images and a coordinate system of the planning image;

using the substantially real time imaging device during the surgical procedure, imaging the region of interest and imaging a portion of a surgical instrument inserted into the patient to generate real time images of the region of interest and real time images of the inserted portion of the surgical instrument;

transforming coordinate positions of the real time images of the surgical instrument into corresponding coordinates of the planning image; and, generating an image representation of said inserted portion of the surgical instrument at corresponding coordinates of the planning image.

14. The method as set forth in claim 13 wherein the step of generating real time images includes generating one of fluoroscopic and continuous CT images.

15. The method as set forth in claim 13 further including:

measuring movement of the surgical instrument in coordinates of a surgical instrument space and converting the coordinates of surgical instrument space into corresponding coordinates in one of the real time image and the planning image for use in generating the image representation of the surgical instrument on the planning image.

16. A medical diagnostic imaging and minimally invasive surgical system comprising:

a surgical instrument which is movable by an operator to any of a plurality of locations adjacent and in a region of interest of a subject;

a system for generating electrical signals indicative of coordinates of the instrument in instrument space;

a three-dimensional diagnostic imaging apparatus for generating three-dimensional diagnostic image data which is indicative of anatomical structure of the region of interest in three-dimensional image space;

a three-dimensional diagnostic image data memory for storing the generated three-dimensional diagnostic image data;

a real time imaging device for imaging the region of interest of the subject and imaging the medical instrument including a portion of the medical instrument inserted into the subject, the real time imaging device generating real time image data of the region of interest of the subject and the medical instrument when the medical instrument is positioned in or adjacent the region of interest in real time image space;

a transform processor for transforming coordinates between the three-dimensional volumetric image space and the real time image space; and, at least one human-readable display connected with the transform processor, the three-dimensional image data memory and the real time imaging device for generating a human-readable display of an image generated from the three-dimensional image data in said three-dimensional volumetric image space with a representation of the surgical instrument transformed from said real time image space to said three-dimensional volumetric image space superimposed thereon.

17. The apparatus as set forth in claim 16 wherein the real time imaging device includes one of a fluoroscopic imaging system and a continuous CT scanner.

18. The apparatus as set forth in claim 16 wherein the real time imaging device includes a C-arm mounted fluoroscopic device which generates fluoroscopic projection images and further including:

first and second fluoroscopic image memories for storing fluoroscopic projection images taken at different angles;

a processor for analyzing the fluoroscopic projection images to determine coordinates of a selected point in fluoroscopic image space, which determined coordinates are supplied to the transform processor to be transformed into corresponding coordinates in three-dimensional image space.

19. The apparatus as set forth in claim 16 wherein the system for determining coordinates of the instrument includes a mechanical arm having a plurality of jointed segments and resolvers for monitoring relative movements of the segments.

20. The apparatus as set forth in claim 16 further including:

a patient support for supporting the patient, the patient support being movable and positioned to move the region of interest between the three-dimensional diagnostic imaging apparatus and the real-time imaging device.

21. The apparatus as set forth in claim 16 wherein:

the real time imaging device and the three-dimensional imaging apparatus are mechanically linked such that each images in parallel planes; and a subject support for moving the subject transversely to the parallel planes.

* * * * *